(12) United States Patent
Maurer, Jr. et al.

(10) Patent No.: US 7,600,405 B2
(45) Date of Patent: Oct. 13, 2009

(54) MICROSURGICAL PROBE

(75) Inventors: Robert S. Maurer, Jr., Huntington Beach, CA (US); Brian D. Burkman, Reinholds, PA (US); Randall R. Martin, Fleetwood, PA (US); Dale E. Ketner, Jr., Sinking Spring, PA (US)

(73) Assignee: Alcon, Inc., Hunenberg (CH)

( * ) Notice: Subject to any disclaimer, the term of this patent is extended or adjusted under 35 U.S.C. 154(b) by 248 days.

(21) Appl. No.: 11/520,316

(22) Filed: Sep. 13, 2006

(65) Prior Publication Data

US 2007/0093793 A1  Apr. 26, 2007

Related U.S. Application Data

(60) Provisional application No. 60/725,526, filed on Oct. 11, 2005.

(51) Int. Cl.
*B21D 17/04* (2006.01)

(52) U.S. Cl. .................... 72/75; 72/80; 72/84; 72/102; 606/107

(58) Field of Classification Search .............. 72/67, 72/69, 75, 80, 112, 115, 118, 120, 121, 123, 72/125, 126, 84, 102; 604/22; 606/4, 107, 606/170, 171
See application file for complete search history.

(56) References Cited

U.S. PATENT DOCUMENTS

| | | | |
|---|---|---|---|
| 1,815,275 A * | 7/1931 | Sadler | 72/126 |
| 2,408,596 A * | 10/1946 | Bednar et al. | 72/69 |
| 2,434,737 A * | 1/1948 | Enghauser | 228/2.3 |
| 2,848,804 A * | 8/1958 | Graves et al. | 72/112 |
| 3,793,863 A * | 2/1974 | Groppini | 72/84 |
| 3,884,238 A | 5/1975 | O'Malley et al. | |
| 4,493,698 A | 1/1985 | Wang et al. | |
| 4,577,629 A | 3/1986 | Martinez | |
| 4,696,298 A | 9/1987 | Higgins et al. | |
| 4,757,814 A | 7/1988 | Wang et al. | |
| 4,819,635 A | 4/1989 | Shapiro | |
| 4,841,984 A | 6/1989 | Armeniades et al. | |
| 4,909,249 A | 3/1990 | Akkas et al. | |
| 4,940,468 A | 7/1990 | Petillo | |
| 4,986,827 A | 1/1991 | Akkas et al. | |
| 5,019,035 A | 5/1991 | Missirlian et al. | |
| 5,020,535 A | 6/1991 | Parker et al. | |
| 5,024,652 A | 6/1991 | Dumenek et al. | |
| 5,047,008 A | 9/1991 | de Juan, Jr. et al. | |
| 5,059,204 A | 10/1991 | Lawson et al. | |
| 5,061,238 A | 10/1991 | Shuler | |
| 5,085,131 A * | 2/1992 | Barrett et al. | 92/169.1 |
| 5,176,628 A | 1/1993 | Charles et al. | |
| 5,235,837 A * | 8/1993 | Werner | 72/69 |
| 5,284,472 A | 2/1994 | Sussman et al. | |
| 5,354,268 A | 10/1994 | Peterson et al. | |

(Continued)

FOREIGN PATENT DOCUMENTS

WO   01/010494 A1   2/2001

(Continued)

*Primary Examiner*—Edward Tolan
(74) *Attorney, Agent, or Firm*—W. David Lee

(57) ABSTRACT

Microsurgical probes having a distal tip with a flat outer surface and a flat inner surface, and methods of forming such probes, are disclosed.

1 Claim, 3 Drawing Sheets

U.S. PATENT DOCUMENTS

| | | | |
|---|---|---|---|
| 5,380,280 A | 1/1995 | Peterson | |
| 5,423,844 A | 6/1995 | Miller | |
| 5,474,532 A | 12/1995 | Steppe | |
| 5,487,725 A | 1/1996 | Peyman | |
| 5,520,652 A | 5/1996 | Peterson | |
| 5,630,827 A | 5/1997 | Vijfvinkel | |
| 5,674,194 A | 10/1997 | Jung et al. | |
| 5,718,139 A * | 2/1998 | Gardner | 72/38 |
| 5,733,297 A | 3/1998 | Wang | |
| 5,782,849 A | 7/1998 | Miller | |
| 5,833,643 A | 11/1998 | Ross et al. | |
| 5,845,527 A * | 12/1998 | Hoffmann et al. | 72/69 |
| 5,893,862 A | 4/1999 | Pratt et al. | |
| 6,010,496 A | 1/2000 | Appelbaum et al. | |
| 6,488,695 B1 | 12/2002 | Hickingbotham | |
| 6,514,268 B2 | 2/2003 | Finlay et al. | |
| 6,575,990 B1 | 6/2003 | Wang et al. | |
| 6,773,445 B2 | 8/2004 | Finlay et al. | |
| 2002/0161398 A1 | 10/2002 | Hickingbotham | |
| 2003/0078609 A1 | 4/2003 | Finlay et al. | |
| 2005/0135776 A1 | 6/2005 | Vijfvinkel | |

FOREIGN PATENT DOCUMENTS

| | | |
|---|---|---|
| WO | 02/058607 A2 | 8/2002 |

\* cited by examiner

MICROSURGICAL PROBE

This application claims the priority of U.S. Provisional Application No. 60/725,526 filed Oct. 11, 2005.

FIELD OF THE INVENTION

The present invention generally pertains to microsurgical probes and more particularly to ophthalmic microsurgical probes such as vitrectomy probes.

DESCRIPTION OF THE RELATED ART

Posterior segment ophthalmic surgical procedures generally require the cutting and/or removal of the vitreous humor, a transparent jelly-like material that fills the posterior segment of the eye. The vitreous humor, or vitreous, is composed of numerous microscopic fibers that are often attached to the retina. Therefore, cutting and removal of the vitreous must be done with great care to avoid traction on the retina, the separation of the retina from the choroid, a retinal tear, or, in the worst case, cutting and removal of the retina itself.

The use of microsurgical cutting probes in posterior segment ophthalmic surgery is well known. Such vitrectomy probes are typically inserted via an incision in the sclera near the pars plana. The surgeon may also insert other microsurgical instruments such as a fiber optic illuminator, an infusion cannula, or an aspiration probe during the posterior segment surgery. The surgeon performs the procedure while viewing the eye under a microscope.

Conventional vitrectomy probes typically include a hollow outer cutting member, a hollow inner cutting member arranged coaxially with and movably disposed within the hollow outer cutting member, and a port extending radially through the outer cutting member near the distal end thereof. Vitreous humor is aspirated into the open port, and the inner member is actuated, closing the port. Upon the closing of the port, cutting surfaces on both the inner and outer cutting members cooperate to cut the vitreous, and the cut vitreous is then aspirated away through the inner cutting member. U.S. Pat. No. 4,577,629 (Martinez); U.S. Pat. No. 5,019,035 (Missirlian et al.); U.S. Pat. No. 4,909,249 (Akkas et al.); U.S. Pat. No. 5,176,628 (Charles et al.); U.S. Pat. No. 5,047,008 (de Juan et al.); 4,696,298 (Higgins et al.); and U.S. Pat. No. 5,733,297 (Wang) all disclose various types of vitrectomy probes, and each of these patents is incorporated herein in its entirety by reference.

During posterior segment ophthalmic surgery, it is generally desirable to remove as much of the overlying vitreous as possible prior to any procedure to repair the underlying retina. However, a surgeon is limited in how close to the retina he or she can dispose a conventional vitrectomy probe due to the geometry of the probe tip and the cutting port. Therefore, a need continues to exist for an improved vitrectomy probe that does not suffer from the above-described limitations.

SUMMARY OF THE INVENTION

One aspect of the present invention is a microsurgical probe. The probe comprises a tubular body having an inner bore, a port providing access to the inner bore, and a closed distal tip. The distal tip has a flat inner surface.

Another aspect of the present invention is a first method of forming a microsurgical probe. A tubular needle is disposed within a collet. The collet and the needle are rotated at high speed. A tool having a generally flat distal surface with a spherical projection thereon is provided. An edge of a distal end of the needle is contacted with the spherical projection. The tool is moved across the distal end of the needle from the edge to slightly past a centerline of the needle so that the distal end of the needle is formed into a closed distal tip having a flat outer surface and a flat inner surface.

Another aspect of the present invention is a second method of forming a microsurgical probe. A distal end of a tubular needle is disposed in contact with a sheet of foil. A compressive force is imparted to the needle and the foil. An electrical impulse is sent between the needle and the foil so that the foil is welded to the needle. The needle is disposed in a punch die, and the needle is punched through the foil so that a closed distal tip having a flat outer surface and a flat inner surface is formed.

BRIEF DESCRIPTION OF THE DRAWINGS

For a more complete understanding of the present invention, and for further objects and advantages thereof, reference is made to the following description taken in conjunction with the accompanying drawings in which.

DETAILED DESCRIPTION OF THE PREFERRED EMBODIMENTS

The preferred embodiments of the present invention and their advantages are best understood by referring to FIGS. 1 through 6 of the drawings, like numerals being used for like and corresponding parts of the various drawings.

Figure 1:
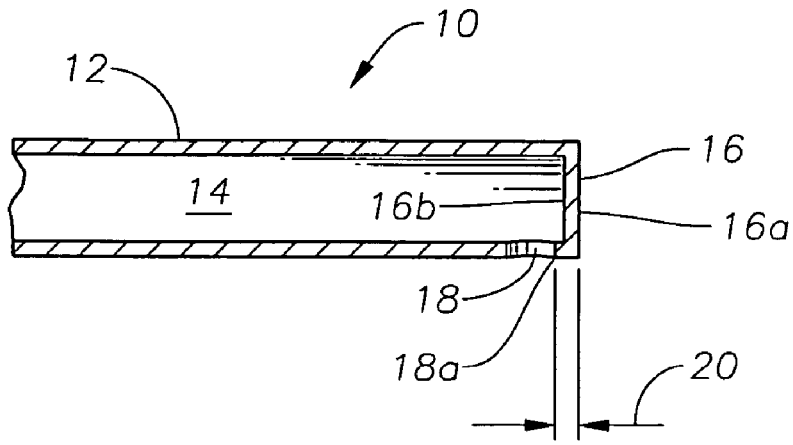
FIG. 1 is a side, sectional, fragmentary view of the distal portion of a vitrectomy probe according to a preferred embodiment of the present invention.

FIG. 1 shows the distal portion of a vitrectomy probe 10 according to a preferred embodiment of the present invention. Probe 10 generally includes a tubular body 12 having an inner bore 14, a closed distal tip 16, and a port 18 providing access to inner bore 14. Tubular body 12 is preferably made of stainless steel. An inner cutting member (not shown) longitudinally reciprocates within inner bore 14 so as to cut tissue aspirated into inner bore 14 via port 18 by a surgical console (not shown). Distal tip 16 has a flat outer surface 16a and a flat inner surface 16b. Probe 10 preferably has a 20 gage to 25 gage diameter.

Figure 2:
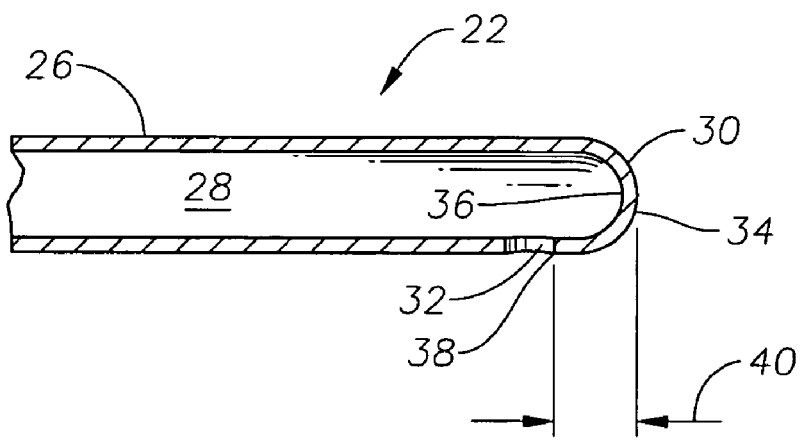
FIG. 2 is a side, sectional, fragmentary view of the distal portion of a conventional vitrectomy probe.
Figure 3:
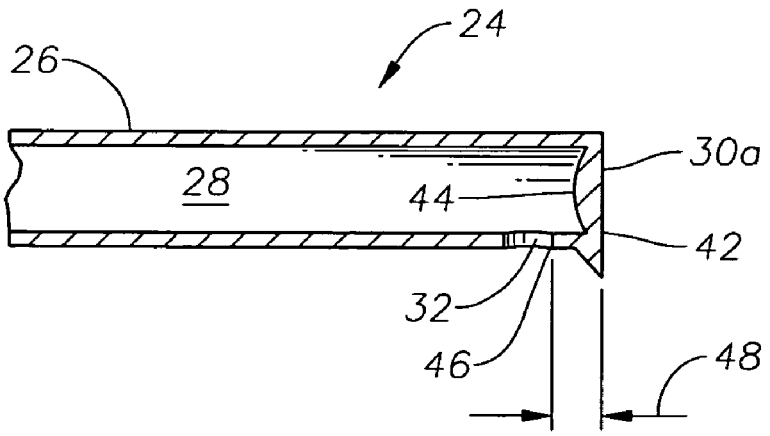
FIG. 3 is a side, sectional, fragmentary view of the distal portion of a second, conventional vitrectomy probe.

FIGS. 2 and 3 show the distal portions of conventional vitrectomy probes 22 and 24, respectively. Probes 22 and 24 each generally include a tubular body 26 having an inner bore 28, closed distal tips 30 and 30a, and a port 32 providing access to inner bore 28. Tubular body 26 is preferably made of stainless steel. An inner cutting member (not shown) longitudinally reciprocates within inner bore 28 so as to cut tissue aspirated into inner bore 28 via port 32 by a surgical console (not shown).

Distal tip 30 has a convex, spherical outer surface 34 and a concave, spherical inner surface 36. Distal tip 30 is manufactured using a conventional spin forming process. In conventional spin forming, tubular needle stock is rotated and a tool having a generally concave distal end is brought into contact with the end of the needle. The force of the tool on the rotating needle closes the end of the tube and creates a distal tip 30 having a spherical geometry.

Distal tip 30a has a flat outer surface 42 and a convex, spherical inner surface 44. Distal tip 30a is manufactured using a conventional bead (or TIG) welding process. In conventional bead welding, an electrode is placed above the end of tubular needle stock and an electric current is passed between the needle and the electrode. A bead of material is formed on the needle end, creating a closed distal tip 30a having a spherical geometry. Secondary machining operations are performed on outer surface 42 to make it flat. However, inner surface 44 retains a convex, spherical shape because the inside weld flash is difficult to control.

As is explained in greater detail hereinbelow, flat outer surface 16a and flat inner surface 16b are preferably formed using an improved spin forming process, or a resistance welding process. Flat outer surface 16a and flat inner surface 16b result in distal end 18a of port 18 being a smaller distance 20 from outer surface 16a than compared to the distance 40 between distal end 38 of port 32 and outer surface 34 of conventional probe 22, or the distance 48 between distal end 46 of port 32 and outer surface 42 of conventional probe 24. Flat inner surface 16b also allows distal end 18a of port 18 to be disposed in a nearly coplanar arrangement with inner surface 16b. In contrast, distal end 38 of port 32 of conventional probe 22 is offset from its inner surface 36 due to the concave, spherical geometry of inner surface 36. Similarly, distal end 46 of port 32 of conventional probe 24 is offset from its inner surface 44 due to the uncertain tolerances of the inside weld flash in the bead welding process. Distance 20 is preferably about 0.006 inches to about 0.016 inches, and is most preferably about 0.006 inches to about 0.011 inches. Distal end 18a of port 18 is preferably disposed about 0.003 inches to about 0.005 inches from inner surface 16b. By minimizing distance 20, a surgeon may dispose probe 10 closer to the retina without contacting the retina. Thus, with probe 10 the surgeon may remove more of the overlying vitreous before performing a procedure to repair the underlying retina than with conventional probes 22 or 24.

Figure 4A:
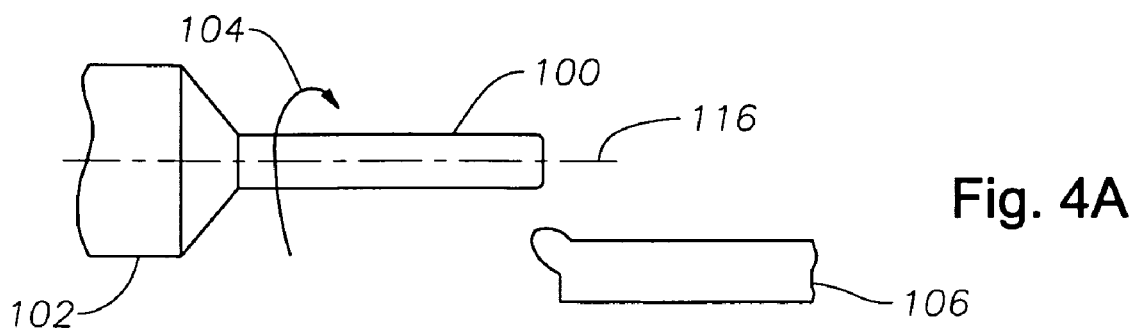
FIGS. 4A-4C schematically illustrate a process to manufacture the vitrectomy probe of FIG. 1 according to a preferred embodiment of the present invention.
Figure 4B:
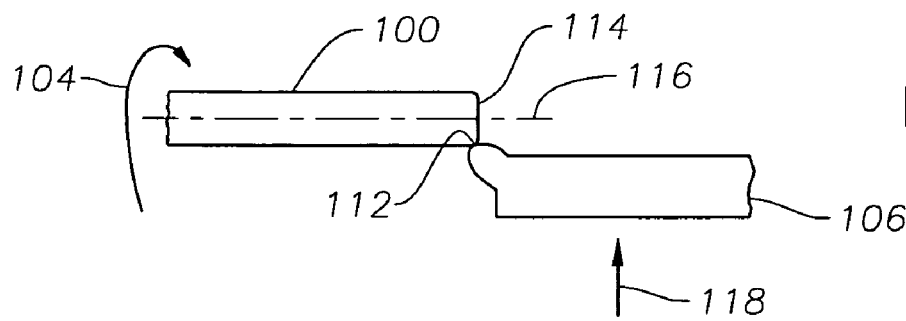
Figure 4C:
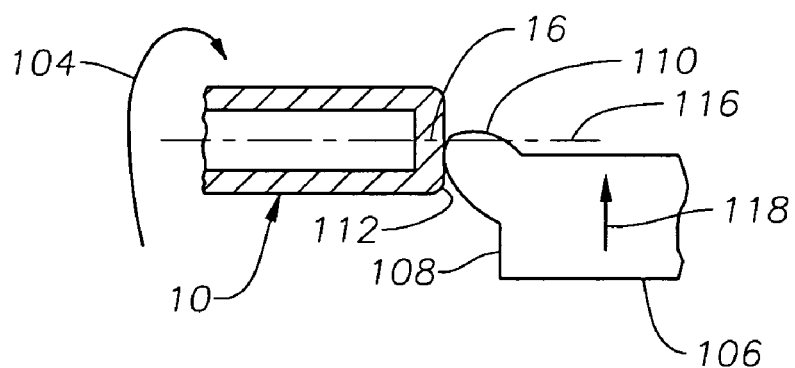
Figure 5:
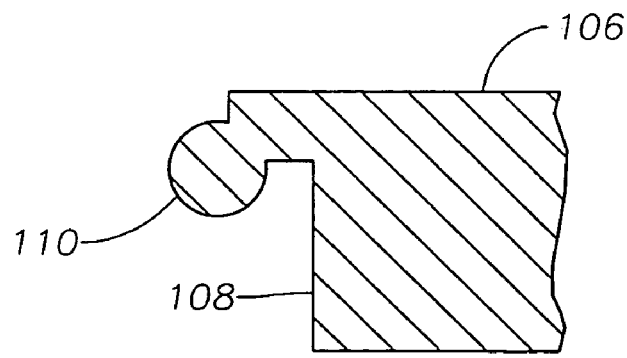
FIG. 5 is a enlarged, fragmentary, sectional, schematic view of a preferred tool for the process of FIGS. 4A-4C.

FIGS. 4A-4C and FIG. 5 schematically illustrate a preferred, improved spin forming process for forming vitrectomy probe 10. Tubular needle stock 100 is disposed within a collet 102 of a lathe (not shown) in the conventional manner. Collet 102, and thus needle 100, are rotated at high speed as indicated by arrow 104. A tool 106, having a generally flat distal surface 108 with a generally spherical projection 110, is brought into contact with an edge 112 of a distal end 114 of needle 100, as shown in FIG. 4B. Tool 106 is moved across the entire face of distal end 114 from edge 112 in the direction of arrow 118. Alternatively, tool 106 is moved across the face of distal end 114 from edge 112 to slightly past a centerline 116 of needle 100 in the direction of arrow 118, as shown in FIG. 4C. The force of projection 110 contacting distal end 114 of needle 100 causes displacement of the material forming needle 100. When projection 110 reaches centerline 116, distal end 114 of needle 100 is closed so as to form distal end 16 of probe 10. The diameter of spherical projection 110 is preferably +/− ten percent of an outer diameter of needle 100. Flat outer surface 16a is preferably machined to have a radius or chamfer on its periphery to facilitate pars plana incision.

Figure 6A:
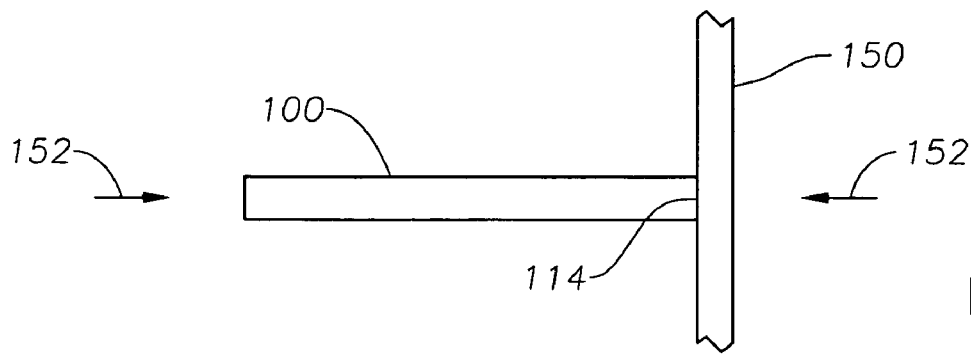
FIGS. 6A-6C schematically illustrate a second process to manufacture the vitrectomy probe of FIG. 1 according to a preferred embodiment of the present invention.
Figure 6B:
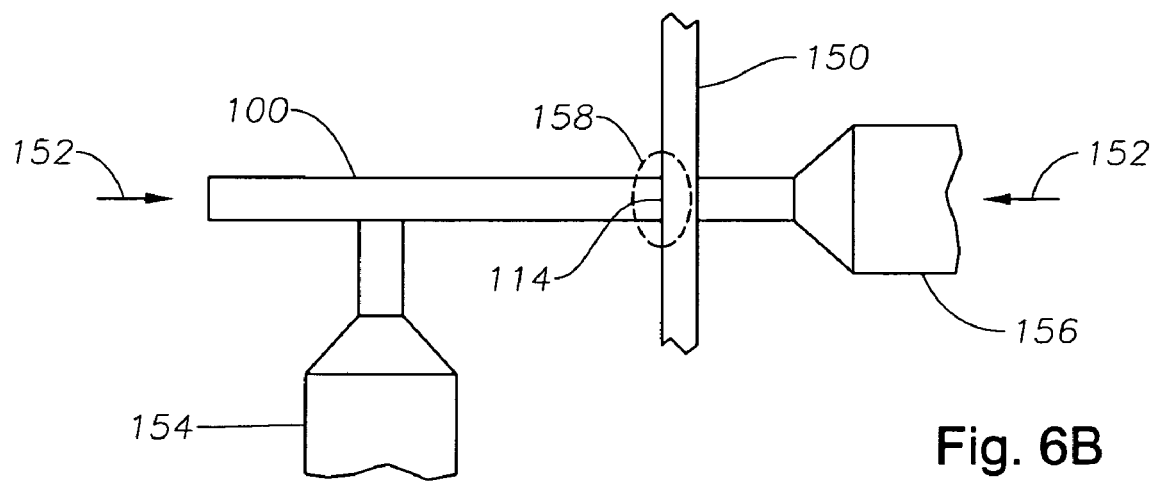
Figure 6C:
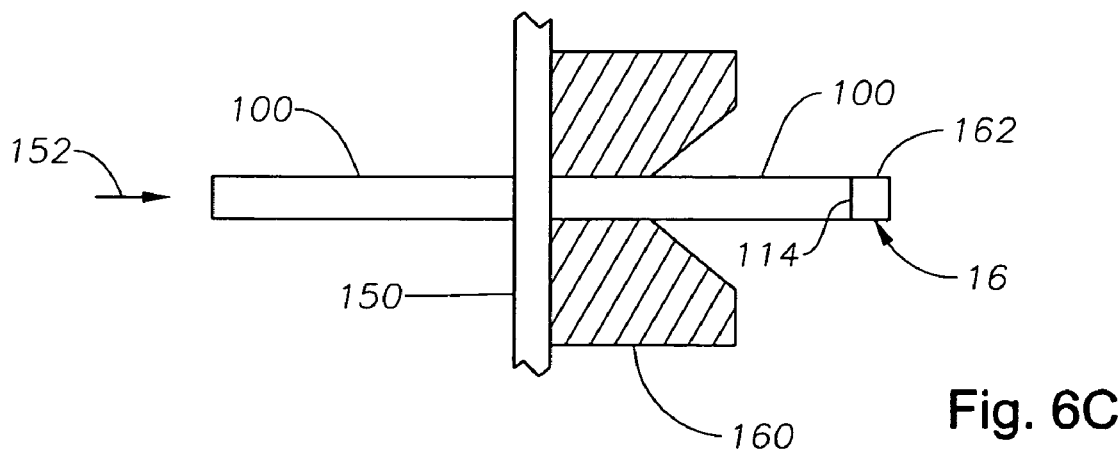

FIGS. 6A-6C schematically illustrate a preferred, resistance welding process for forming vitrectomy probe 10. Distal end 114 of tubular needle stock 100 is brought into contact with a sheet of stainless steel foil 150, and a compressive force indicated by arrows 152 is placed on needle 100 and foil 150. Foil 150 preferably has a thickness of about 0.004 inches. An electrode 154 is disposed on a side of needle 100, and an electrode 156 is disposed on foil 150. An electrical impulse is sent between electrodes 154 and 156. As the electrical impulse moves from needle 100 to foil 150, a localized area of high resistance is encountered that generates heat and welds distal end 114 to foil 150 in a melt zone 158. Needle 100 is disposed in a punch die 160, and needle 100 is then punched through foil 150 (as shown in FIG. 6C) so that welded foil tip 162 forms distal end 16 of probe 10. A preferred resistance welding machine is the Model 125 resistance welding machine available from Miyachi Unitek Corporation of Monrovia, Calif. A micro welding head available from Miyachi Unitek Corporation, which contains electrode 156, is preferably used with the Model 125 resistance welding machine. A preferred weld cycle is a dual pulse cycle within the ten percent (10%) to sixty percent (60%) power range. Flat outer surface 16a is preferably machined to have a radius or chamfer on its periphery to facilitate pars plana incision.

From the above, it may be appreciated that the present invention provides improved apparatus and methods of performing vitrectomy surgery. The present invention is illustrated herein by example, and various modifications may be made by a person of ordinary skill in the art. For example, although the present invention is described herein in connection with a vitrectomy probe, it is applicable to other ophthalmic microsurgical probes and non-ophthalmic micrsosurgical probes. As another example, although the present invention is described herein in connection with a cutting probe, it is also applicable to an aspiration probe.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A method of forming a vitrectomy probe, comprising:
disposing a tubular needle within a collet;
rotating said collet and said needle at high speed;
providing a tool having a generally flat distal surface with a convex spherical projection extending from said generally flat distal surface;
contacting an edge of a distal end of said needle with said convex, spherical projection; and
moving said tool across said distal end of said needle from said edge to slightly past a centerline of said needle so that said distal end of said needle is formed into a closed distal tip having a flat outer surface and a flat inner surface.

* * * * *

UNITED STATES PATENT AND TRADEMARK OFFICE
CERTIFICATE OF CORRECTION

PATENT NO. : 7,600,405 B2  Page 1 of 1
APPLICATION NO. : 11/520316
DATED : October 13, 2009
INVENTOR(S) : Maurer, Jr. et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 278 days.

Signed and Sealed this

Fifth Day of October, 2010

David J. Kappos
*Director of the United States Patent and Trademark Office*